(12) United States Patent
Mougin et al.

(10) Patent No.: US 7,906,126 B2
(45) Date of Patent: *Mar. 15, 2011

(54) ADHESIVE BLOCK ETHYLENIC COPOLYMERS, COSMETIC COMPOSITIONS CONTAINING THEM AND COSMETIC USE OF THESE COPOLYMERS

(75) Inventors: Nathalie Mougin, Paris (FR); Bertrand Lion, Luzarches (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/516,613

(22) Filed: Sep. 7, 2006

(65) Prior Publication Data

US 2007/0003506 A1  Jan. 4, 2007

Related U.S. Application Data

(63) Continuation of application No. 10/304,793, filed on Nov. 27, 2002.

(60) Provisional application No. 60/367,728, filed on Mar. 28, 2002.

(30) Foreign Application Priority Data

Nov. 29, 2001 (FR) ...................... 01 15436

(51) Int. Cl.
*A61K 8/02* (2006.01)
*A61K 8/00* (2006.01)
*A61K 8/18* (2006.01)
*A61K 8/72* (2006.01)
*A61K 8/73* (2006.01)
*A61K 8/81* (2006.01)
*A61K 9/14* (2006.01)
*A61K 31/74* (2006.01)

(52) U.S. Cl. ............... 424/401; 424/59; 424/60; 424/61; 424/63; 424/70.1; 424/70.11; 424/70.15; 424/70.16; 424/70.17; 424/70.27; 424/78.02; 424/78.03; 424/78.18; 424/486; 424/487; 514/844; 514/881

(58) Field of Classification Search .................... 424/401
See application file for complete search history.

(56) References Cited

U.S. PATENT DOCUMENTS

| 4,030,512 | A | 6/1977 | Papantoniou et al. |
| 4,282,203 | A | 8/1981 | Jacquet et al. |
| 4,726,942 | A | 2/1988 | Lang et al. |
| 5,264,527 | A | 11/1993 | Varshney et al. |
| 5,290,842 | A * | 3/1994 | Sasaki et al. ............. 524/271 |
| 5,314,962 | A | 5/1994 | Otsu et al. |
| 5,711,940 | A | 1/1998 | Kuentz et al. |
| 5,763,548 | A | 6/1998 | Matyjaszewski et al. |
| 5,807,937 | A | 9/1998 | Matyjaszewski et al. |
| 6,153,705 | A | 11/2000 | Corpart et al. |
| 6,239,226 | B1 | 5/2001 | Fischer et al. |
| 6,288,173 | B1 | 9/2001 | Schimmel et al. |
| 6,361,768 | B1 * | 3/2002 | Galleguillos et al. ...... 424/70.12 |
| 6,538,091 | B1 | 3/2003 | Matyjaszewski et al. |
| 6,663,855 | B2 * | 12/2003 | Frechet et al. ............. 424/70.11 |
| 6,685,925 | B2 * | 2/2004 | Frechet et al. ............. 424/70.16 |
| 6,805,872 | B2 | 10/2004 | Mougin |
| 6,864,314 | B1 | 3/2005 | Yeung et al. |
| 7,307,115 | B2 | 12/2007 | Husemann et al. |
| 2002/0011578 | A1 | 1/2002 | Gardner |
| 2003/0124074 | A1 * | 7/2003 | Mougin et al. .................. 424/61 |
| 2005/0020779 | A1 | 1/2005 | Mougin et al. |
| 2005/0090592 | A1 | 4/2005 | Husemann et al. |
| 2007/0003506 | A1 | 1/2007 | Mougin et al. |
| 2007/0003507 | A1 * | 1/2007 | Mougin et al. ............. 424/70.16 |
| 2008/0159965 | A1 * | 7/2008 | Mougin et al. .................. 424/45 |

FOREIGN PATENT DOCUMENTS

| DE | 196 02 540 | 7/1997 |
| EP | 0 266 062 | 5/1988 |
| EP | 0 921 170 | 6/1999 |
| EP | 1141056 | 10/2001 |
| FR | 2 439 798 | 5/1980 |
| FR | 2 746 640 | 7/1997 |
| JP | 10-008011 | 1/1998 |
| JP | 11-116644 | 4/1999 |
| JP | 2000-500516 | 1/2000 |
| JP | 2001-200026 | 7/2001 |
| JP | 2001-348553 | 12/2001 |
| JP | 2002-534540 | 10/2002 |
| JP | 2003-500496 | 1/2003 |
| JP | 2003-534264 | 11/2003 |
| JP | 2004-505166 | 2/2004 |
| WO | WO 97/18247 | 5/1997 |
| WO | WO 98/58974 | 12/1998 |
| WO | WO 00/40628 | 7/2000 |
| WO | WO 00/71591 | 11/2000 |

(Continued)

OTHER PUBLICATIONS

Polymer Products from Aldrich, p. 52-53, obtained from the web in 2010 at http://www.sigmaaldrich.com/etc/medialib/docs/Aldrich/General_Information/thermal_transitions_of_homopolymers. Par.0001.File.tmp/thermal_transitions_of_homopolymers.pdf.*

(Continued)

*Primary Examiner* — Johann R Richter
*Assistant Examiner* — Nathan W Schlientz
(74) *Attorney, Agent, or Firm* — Oblon, Spivak, McClelland, Maier & Neustadt, L.L.P.

(57) ABSTRACT

A cosmetic composition of a linear, block ethylenic copolymer dissolved in a physiologically acceptable medium where the linear, block ethylenic copolymer includes at least two blocks having different glass transition temperatures, Tg; and one of the blocks is a copolymer of different monomers chosen from acrylates and/or methacrylates.

27 Claims, No Drawings

FOREIGN PATENT DOCUMENTS

| WO | WO-A1-00 71591 | 11/2000 |
|----|----------------|---------|
| WO | WO-A1-01 89470 | 11/2001 |
| WO | WO 02/10309    | 2/2002  |

OTHER PUBLICATIONS

T.P. Davis, et al., New Methods of Polymer Synthesis, vol. 2, pp. 1-36, "Recent Developments in Radical Polymerization", 1995.

Jin-Shan Wang, et al., J. American Chemical Society, vol. 117, No. 20, pp. 5614-5615, "Controlled Living Radical Polymerization. Atom Transfer Radical Polymerization in the Presence of Transition Metal Complexes", 1995.

S. Kobatake, et al., Macromolecules, vol. 30, No. 14, pp. 4238-4240, "Synthesis of Nitroxy-Functionalized Polybutadiene by Anionic Polymerization Using a Nitroxy-Functionalized Terminator", 1997.

E.E. Malmstrom, et al., Macromol. Chem. Phys. vol. 199, No. 6, pp. 923-935, "Macromolecular Engineering Via Living Free Radical Polmerizations", Jun. 1998.

U.S. Appl. No. 12/041,693, filed Mar. 4, 2008, Mougin, et al.

* cited by examiner

ADHESIVE BLOCK ETHYLENIC COPOLYMERS, COSMETIC COMPOSITIONS CONTAINING THEM AND COSMETIC USE OF THESE COPOLYMERS

The present invention relates to novel polymers of specific structure of the adhesive block ethylenic copolymer type.

The present invention also relates to a composition, especially a cosmetic or pharmaceutical composition, in particular a hair composition, comprising the said polymer of specific structure.

The invention also relates to the cosmetic use of these polymers for treating the skin, the nails or the hair.

The hairstyling compositions that are currently the most widespread on the cosmetics market for shaping and/or holding the hairstyle are styling gels and mousses or sprays.

These compositions contain one or more polymer resins, one of the functions of which is to create links between the hairs. These compounds are also known as fixers and are mixed with various cosmetic additives.

Moreover, vinyl polymers with high glass transition temperatures are known in cosmetics from document FR-A-2 439 798 and are especially included in styling compositions.

In the field of styling compositions, although such polymers allow holding of the hairstyle, they have the drawback of being excessively brittle, which does not allow good hold of the hairstyle over time.

To overcome this brittle nature, the polymers are generally plasticized with plasticizers, but these plasticizers impair the styling properties of the polymer.

There is thus a need for a polymer which, when included in a composition, in particular a cosmetic composition, allows this composition not to have the drawbacks, limitations, defects and disadvantages of the compositions of the prior art.

Especially, such a polymer must, in a composition for treating the hair, give greater hold while maintaining a natural effect. In a two-coat composition for treating the nails, it must allow good adhesion of the first coat, and finally, in a composition for treating the skin, it must allow the makeup to adhere to the skin, while being comfortable and non-sticky, without making the skin taut.

The aim of the present invention is to provide a polymer that satisfies, inter alia, the needs, criteria and requirements mentioned above and that solves the problems of the polymers of the prior art.

This aim and others are achieved, in accordance with the present invention, by a linear block ethylenic copolymer, comprising:
- at least two blocks having different glass transition temperatures (Tg);
- at least one of these blocks having a glass transition temperature of less than or equal to 20° C.;
- the said copolymer also having an adhesion or "tack" value of greater than 1N.

A subject of the invention is also cosmetic compositions comprising the said linear block ethylenic copolymers.

When they are incorporated into cosmetic compositions, the copolymers having the specific structure according to the invention make it possible to obtain extremely advantageous properties, which it would not be possible to obtain with the polymers of the prior art. In general, these polymers have an adhesive nature and they thus lead to compositions or systems with improved hold and adhesion.

Thus, when the copolymers according to the invention are used in compositions for treating the hair, such as lacquers or shampoos, they give greater hold, while maintaining a natural effect. In compositions for treating the nails, such as nail varnishes, they increase the adhesion of the first coat. In compositions for treating the skin, i.e. in a wide variety of makeup compositions, the copolymers according to the invention improve the adhesion to the skin, give a comfortable sensation, do not feel sticky and do not make the skin taut.

The invention also relates to a cosmetic process for making up or caring for maquillage keratin materials, comprising the application to the keratin materials of a cosmetic composition according to the invention.

The invention thus also relates to the use of the copolymers according to the invention to improve the styling power and hold of a hair lacquer, the use of the copolymers to improve the adhesion of a nail varnish, and lastly the use of the copolymers to improve the hold and adhesion of a makeup composition.

The copolymers of the invention thus provide a solution to the problems posed by the polymers of the prior art.

The unexpected advantageous properties of the specific copolymers of the invention, which are fundamentally linear polymers, arise firstly from this linear nature and secondly from the specific nature of the blocks of which they are made.

Specifically, the blocks in the copolymers of the invention are defined by particular glass transition temperatures. There was nothing in the prior art to suggest that by using a specifically linear copolymer, and by setting defined Tg conditions for the blocks of which the copolymer is made, it would be possible to obtain, according to the invention, a combination of excellent properties for the copolymer.

Without wishing to be bound by any theory, the advantageous properties of the copolymer according to the invention are considered to arise from the fact that the specific structure and the specific choice of the blocks of which it is made promote the phase separation between the blocks.

More specifically, the linear copolymers of the present invention are defined as being ethylenic copolymers. This means that the monomers from which the blocks that make up this copolymer are derived are monomers containing a carbon-carbon unsaturated double bond of ethylenic type.

In addition, specifically, the copolymer according to the invention is a linear copolymer. This means that the invention is not intended to cover copolymers having a non-linear structure, for example branched, starburst, grafted or the like. The linear nature of the copolymers of the invention is important for giving the compositions containing it the advantageous properties described above.

Advantageously, the copolymer according to the invention is a film-forming polymer, i.e. it is capable by itself, or in the presence of an auxiliary film-forming agent, at a temperature ranging from 20° C. to 30° C., of forming a continuous (to the naked eye) film that adheres to a keratin support.

According to the invention, the copolymer comprises at least two blocks that have different glass transition temperatures (Tg), and also at least one of these blocks of the copolymer has a glass transition temperature of less than or equal to 20° C.

Since the glass transition temperature Tg is an essential parameter for defining the blocks in the copolymer of the invention and, consequently, the copolymer of the invention, it is important to point out that the glass transition temperatures of the blocks in the copolymers used in the present invention are measured by differential scanning calorimetry for the dry polymer, at a heating rate of 10° C./minute.

The copolymers according to the invention are also defined by a specific mechanical criterion, which is the "adhesion" or "tack". According to the invention, the copolymers have an adhesion or tack that is generally greater than 1N, preferably greater than 2N and more preferably greater than 3N.

This "adhesion" or "tack", defined by Fmax, is measured by the following test.

Fmax is the maximum tensile force, measured using an extensometer, required to detach the respective surfaces, with an area of 0.95 cm², of two rigid, inert, non-absorbent glass supports (A) and (B) placed face to face. The said surfaces were precoated with a composition comprising the copolymer to be tested, according to the invention, this coating composition has a solids concentration (C) of 10% (in grams per 100 grams of composition), and the surfaces of the supports are coated at a rate of 4/C mg/cm².

The surfaces are then dried for 48 hours at 22° C., under a relative humidity of 50%, and are then subjected for 20 seconds to a compression of 3 newtons and finally subjected for 60 seconds to traction, at a speed of 10 mm/minute.

Each block in the copolymer according to the invention is derived from one type of monomer or from several different types of monomer.

This means that each block may consist of a homopolymer or a copolymer; this copolymer of which the block is made may in turn be random or alternating.

According to the invention, the copolymer comprises at least two blocks, having different glass transition temperatures (Tg). Advantageously, the difference in glass transition temperatures between these two blocks, having different glass transition temperatures, is generally from 40 to 120° C., preferably from 40 to 110° C. and more preferably from 40° C. to 100° C.

The number-average mass of the copolymer is generally from 10,000 to 500,000 and preferably from 50,000 to 200,000.

Advantageously, the proportion of the block with a Tg of less than or equal to 20° C. is from 99% to 40% of the polymer, preferably from 95% to 55% and more preferably from 90% to 50%.

Advantageously, the block with a Tg of less than or equal to 20° C. has a temperature Tg from 20 to −100° C., preferably from 20 to −95° C. and more preferably from 20 to −90° C.

The block whose glass transition temperature is less than or equal to 20° C., which is a homopolymer or a copolymer, is preferably totally or partly derived from one or more monomers, which are such that the homopolymers prepared from these monomers have glass transition temperatures of less than or equal to 20° C.

More preferably, the block whose glass transition temperature is less than or equal to 20° C. is a homopolymer consisting of a single type of monomer (the Tg of the corresponding homopolymer of which is less than 20° C.).

The monomers whose homopolymers have glass transition temperatures of less than or equal to 20° C. and from which is(are) preferably derived the block(s) of Tg≦20° C. of the copolymer of the invention are preferably chosen from the following monomers:
ethylenic hydrocarbons of 2 to 10 C, such as ethylene, isoprene and butadiene;
acrylates of formula CH₂=CHCOOR₁, R₁ representing a linear or branched 1 to 12 C alkyl group, in which one or more hetero atoms chosen from O, N and S is(are) optionally inserted, the said alkyl group also possibly being optionally substituted with one or more substituents chosen from hydroxyl groups and halogen atoms (Cl, Br, I and F);
examples of groups R₁ are methyl, ethyl, propyl, butyl, isobutyl, hexyl, ethylhexyl, octyl, lauryl, isooctyl, iso-decyl, hydroxyethyl, hydroxypropyl, methoxyethyl, ethoxyethyl and methoxypropyl groups,
another example of R₁ for the acrylates are POE (polyoxyethylene)—C₁ to C₁₂ alkyl groups, with repetition of the oxyethylene unit from 5 to 30 times, for example methoxy POE, i.e. the groups R₁=R"—(OC₂H₄)ₙ—, with R"=C₁-C₁₂ alkyl and n=5 to 30,
R₁ may also denote a polyoxyethylene group comprising from 5 to 30 ethylene oxide units;
the methacrylates of formula:

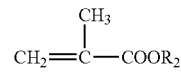

R₂ representing a linear or branched 3 to 12 C alkyl group, in which one or more hetero atoms chosen from O, N and S is(are) optionally inserted, the said alkyl group possibly also being optionally substituted with one or more substituents chosen from hydroxyl groups and halogen atoms (Cl, Br, I and F); examples of groups R₂ are hexyl, ethylhexyl, octyl, lauryl, isooctyl, isodecyl, dodecyl, methoxyethyl, methoxypropyl, ethoxyethyl, POE (polyoxyethylene with repetition of the oxyethylene unit from 5 to 30 times) and (C₁ to C₃₀) alkyl-POE (with repetition of the oxyethylene unit from 5 to 30 times);
the vinyl esters of formula:

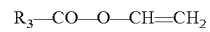

in which R₃ represents a linear or branched 2 to 12 C alkyl group;
examples of such vinyl esters are: vinyl propionate, vinyl butyrate, vinyl ethylhexanoate, vinyl neononanoate and vinyl neodecanoate;
vinyl ethers of a 1 to 12 C alkyl, such as methyl vinyl ether and ethyl vinyl ether;
N-(1 to 12 C)alkyl acrylamides, such as N-octylacrylamide.

The monomers that are particularly preferred are: n-butyl acrylate, ethylhexyl acrylate, isobutyl acrylate, methoxyethyl acrylate, ethoxyethyl (meth)-acrylate and n-hexyl (meth) acrylate.

The block with a glass transition temperature of less than or equal to 20° C. can, besides the monomers indicated above, and the glass transition temperature Tg of the corresponding homopolymer of which is less than or equal to 20° C., comprise one or more other different monomers known as additional monomers.

This or these additional monomer(s) is(are) obviously chosen such that the Tg of the block is less than or equal to 20° C.

Thus, a block of adequate Tg, less than or equal to 20° C., may be formed from a copolymer consisting of a first monomer for which the Tg of the corresponding homopolymer is in the range from more than 20° C. to 200° C. and preferably from more than 20° C. to 120° C., and of a second monomer for which the Tg of the corresponding homopolymer is in the range from 20° C. to −100° C.

For example, it will be possible to combine in the copolymer forming the block a monomer with a Tg (of the corresponding homopolymer) equal to 100° C., in a proportion of 35% by weight relative to the total weight of monomers, and a monomer with a Tg equal to −70° C., in a proportion of 65% by weight, and the resulting block will have a Tg of −30° C.

These additional monomers which thus have a Tg for the equivalent homopolymer of greater than 20° C. are chosen especially from acrylates, methacrylates, meth(acrylamide), vinyl and allylic compounds, etc.

The additional monomers (with a Tg for the corresponding homopolymer >20° C.) are preferably chosen from the following monomers:

the vinyl compounds of formula:

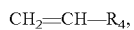

in which $R_4$ is a hydroxyl group; a group

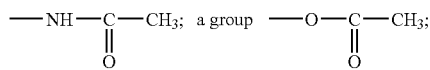

a $C_3$ to $C_8$ cycloalkyl group; a $C_6$ to $C_{20}$ aryl group; a $C_7$ to $C_{30}$ aralkyl group ($C_1$ to $C_4$ alkyl); a 4- to 12-membered heterocyclic group containing one or more hetero atoms chosen from O, N and S; a heterocyclyl-alkyl group ($C_1$ to $C_4$ alkyl) such as a furfuryl group; the said cycloalkyl, aryl, aralkyl, heterocyclic or heterocyclylalkyl groups possibly being optionally substituted with one or more substituents chosen from hydroxyl groups, halogen atoms and linear or branched 1 to 4 C alkyl groups in which is(are) optionally inserted one or more hetero atoms chosen from O, N, S and P, and the said alkyl groups also possibly being optionally substituted with one or more substituents chosen from hydroxyl groups and halogen atoms (Cl, Br, I and F).

Examples of vinyl monomers are vinylcyclohexane, styrene and vinyl acetate.

The acrylates of formula:

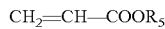

in which $R_5$ is a tert-butyl group; a $C_3$ to $C_8$ cycloalkyl group; a $C_6$ to $C_{20}$ aryl group; a $C_7$ to $C_{30}$ aralkyl group ($C_1$ to $C_4$ alkyl); a 4- to 12-membered heterocyclic group containing one or more hetero atoms chosen from O, N and S; a heterocyclylalkyl group ($C_1$ to $C_4$ alkyl), such as a furfuryl group; the said cycloalkyl, aryl, aralkyl, heterocyclic or hetero-cyclylalkyl groups possibly being optionally substituted with one or more substituents chosen from hydroxyl groups, halogen atoms and linear or branched 1 to 4 C alkyl groups in which is(are) optionally inserted one or more hetero atoms chosen from O, N, S and P, the said alkyl groups also possibly being optionally substituted with one or more substituents chosen from hydroxyl groups and halogen atoms (Cl, Br, I and F).

Examples of acrylate monomers are t-butylcyclohexyl acrylate, tert-butyl acrylate, t-butylbenzyl acrylate, furfuryl acrylate and isobornyl acrylate;

the methacrylates of formula:

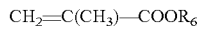

in which $R_6$ is a linear or branched 1 to 4 C alkyl group, such as a methyl, ethyl, propyl or isobutyl group, the said alkyl group also possibly being optionally substituted with one or more substituents chosen from hydroxyl groups and halogen atoms (Cl, Br, I and F); a $C_3$ to $C_8$ cycloalkyl group; a $C_6$ to $C_{20}$ aryl group; a $C_7$ to $C_{30}$ aralkyl group ($C_1$ to $C_4$ alkyl group); a 4- to 12-membered heterocyclic group containing one or more hetero atoms chosen from O, N and S; a heterocyclylalkyl group (1 to 4 C alkyl), such as a furfuryl group; the said cycloalkyl, aryl, aralkyl or heterocyclic or heterocyclylalkyl groups possibly being optionally substituted with one or more substituents chosen from hydroxyl groups, halogen atoms and linear or branched 1 to 4 C alkyl groups in which is(are) optionally inserted one or more hetero atoms chosen from O, N, S and P, the said alkyl groups also possibly being optionally substituted with one or more substituents chosen from hydroxyl groups and halogen atoms (Cl, Br, I and F).

Examples of methacrylate monomers are methyl methacrylate, ethyl methacrylate, n-butyl methacrylate, isobutyl methacrylate, t-butylcyclohexyl methacrylate, t-butylbenzyl methacrylate, methoxyethyl methacrylate, methoxypropyl methacrylate and isobornyl methacrylate;

the (meth)acrylamides of formula:

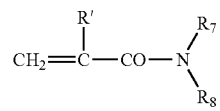

in which $R_7$ and $R_8$, which may be identical or different, each represent a hydrogen atom or a linear or branched alkyl group of 1 to 12 carbon atoms, such as an n-butyl, t-butyl, isopropyl, isohexyl, isooctyl or isononyl group, and R' denotes H or methyl.

Examples of (meth)acrylamide monomers are N-butylacrylamide, N-t-butylacrylamide, N-isopropyl-acrylamide, N,N-dimethylacrylamide and N,N-dibutyl-acrylamide. The monomers that are preferred among all those mentioned above are chosen from furfuryl acrylate, isobornyl acrylate, tert-butyl acrylate, tert-butylcyclohexyl acrylate, tert-butylbenzyl acrylate, methyl methacrylate, n-butyl methacrylate, ethyl methacrylate, isobutyl methacrylate, styrene, vinyl acetate and vinylcyclohexane.

Examples of these additional monomers that are particularly preferred are methyl methacrylate, styrene, (meth)acrylic acid, isobornyl acrylate and furfuryl acrylate.

This or these additional monomer(s) is(are) generally present in an amount of less than or equal to 50% by weight, preferably less than or equal to 45% by weight and more preferably less than or equal to 40% by weight relative to the total weight of the block with a Tg of less than or equal to 20° C.

Advantageously, the copolymer according to the invention comprises at least one hydrophilic block which comprises hydrophilic monomers.

The hydrophilic block may be defined as being a water-soluble or water-dispersible block.

The polymer forming the block is water-soluble if it is soluble in water to a proportion of at least 5% by weight, at 25° C.

The polymer forming the block is water-dispersible if it forms, at a concentration of 5% and at 25° C., a stable suspension of fine, generally spherical particles. The mean size of the particles constituting the said dispersion is less than 1 μm and more generally ranges between 5 and 400 nm and preferably from 10 to 250 nm. These particle sizes are measured by light scattering.

The hydrophilic block is preferably a block whose glass transition temperature is greater than 20° C. but it may also be a block whose glass transition temperature is less than or equal to 20° C.

It is known that the hydrophilic monomers whose homopolymers have a glass transition temperature of less than 20° C. are not common.

Accordingly, when the hydrophilic block is a block with a Tg of less than or equal to 20° C., it is advantageously a copolymer.

This hydrophilic block then advantageously comprises one or more hydrophilic monomer(s) whose corresponding homopolymers have glass transition temperatures of greater than 20° C. and one or more other non-hydrophilic monomer(s) chosen especially from those whose homopolymers have Tg values of less than or equal to 20° C.

The proportion of the various hydrophilic and non-hydrophilic monomers is preferably chosen such that the whole block consisting of a copolymer has a Tg of greater than 20° C.

When the hydrophilic block has a glass transition temperature of greater than 20° C., it generally comprises from 70% to 100% and preferably from 80% to 100% of hydrophilic monomers for which the Tg values of the corresponding homopolymers are greater than 20° C.

When the hydrophilic block has a glass transition temperature of less than or equal to 20° C., it generally comprises from 10% to less than 70% and preferably from 20% to 65% of hydrophilic monomers for which the Tg values of the corresponding homopolymers are greater than 20° C.

Examples of hydrophilic monomers for which the Tg of the corresponding homopolymer is greater than 20° C. include cationic monomers, anionic monomers and nonionic monomers.

Examples of cationic monomers are:
2-vinylpyridine;
4-vinylpyridine;
dimethylaminoethyl methacrylate (DMAEMA);
diethylaminoethyl methacrylate (DEAEMA);
dimethylaminopropylacrylamide; and
the salts thereof, whether they are salts of mineral acids, such as sulphuric acid or hydrochloric acid, or salts of organic acids.

These organic acids may comprise one or more carboxylic, sulphonic or phosphonic groups. They may be linear, branched or cyclic aliphatic acids or alternatively aromatic acids. These acids may also comprise one or more hetero atoms chosen from O and N, for example in the form of hydroxyl groups.

An example of an acid containing an alkyl group is acetic acid $CH_3COOH$.

An example of a polyacid is terephthalic acid.

Examples of hydroxy acids are citric acid and tartaric acid.

Examples of anionic monomers are:
acrylic acid, methacrylic acid, crotonic acid, maleic anhydride, itaconic acid, fumaric acid and maleic acid;
styrenesulphonic acid, acrylamidopropanesulphonic acid, vinylbenzoic acid, vinylphosphonic acid and the salts thereof.

The neutralizer may be a mineral base, such as LiOH, NaOH, KOH, $Ca(OH)_2$ or $NH_4OH$, or an organic base, for example a primary, secondary or tertiary amine, such as a primary alkylamine, for instance 2-amino-2-methylpropanol, or a secondary or tertiary alkylamine.

Examples of nonionic monomers are:
hydroxyalkyl(meth)acrylates in which the alkyl group contains from 2 to 4 C atoms, in particular hydroxyethyl (meth)acrylate,
vinyllactams, (meth)acrylamides and N—($C_1$-$C_4$)-alkyl (meth)acrylamides, for instance isobutylacrylamide; and polysaccharide(meth)acrylates, for instance sucrose acrylate.

It should be noted that even though the copolymer comprises a hydrophilic block, the overall copolymer is not necessarily hydrophilic.

The linear block ethylenic copolymers according to the invention are chosen from:
diblock copolymers;
triblock copolymers;
multiblock copolymers containing more than three blocks.

In the case of multiblock copolymers, in which one or two blocks satisfy the criterion of a Tg of less than or equal to 20° C. The other blocks then have a Tg of greater than 20° C. and less than 200° C.

For example, the copolymers may comprise two blocks having a Tg≦20° C. and one or two blocks having a Tg>20° C.

The copolymers according to the invention may be prepared by anionic polymerization.

Preferably, however, the copolymers according to the invention are obtained, in a first mode, by controlled free-radical polymerization, but they may also be obtained, according to a second mode, by standard free-radical polymerization.

First Mode:

The block copolymers according to the invention are preferably obtained by controlled free-radical polymerization, described especially in "New Method of Polymer Synthesis", Blackie Academic & Professional, London, 1995, Volume 2, page 1.

Controlled free-radical polymerization makes it possible to reduce the deactivation reactions of the growing free-radical species, in particular the termination step, these being reactions which, in standard free-radical polymerization, irreversibly and uncontrollably stop the growth of the polymer chain.

In order to reduce the probability of termination reactions, it has been proposed to temporarily and reversibly block the growing free-radical species, by forming "dormant" active species in the form of a bond with a low dissociation energy.

Thus, the polymerization may be carried out according to the atom transfer technique, or by reaction with a nitroxide, or alternatively according to the "reversible addition-fragmentation chain-transfer" technique.

The atom-transfer free-radical polymerization technique, also known by the abbreviation ATRP, consists in blocking the growing free-radical species in the form of a bond of C-halide type (in the presence of a metal/ligand complex). This type of polymerization is reflected by control of the mass of the polymers formed and by a low polydispersity index.

In general, the atom-transfer free-radical polymerization is performed by polymerizing one or more polymerizable monomers via a free-radical route, in the presence of:
an initiator containing at least one transferable halogen atom;
a compound comprising a transition metal capable of participating in a reduction step with the initiator and a "dormant" polymer chain; and
a ligand that may be chosen from compounds comprising a nitrogen (N), oxygen (O), phosphorus (P) or sulphur (S) atom, which may be coordinated by a σ bond to the said compound comprising a transition metal, the formation of direct bonds between the said compound comprising a transition metal and the polymer in formation being avoided.

The halogen atom is preferably a chlorine or bromine atom.

This process is described in particular in patent application WO 97/18247 and in the article by Matyjasezwski et al., published in JACS, 117, page 5614 (1995).

The technique of free-radical polymerization by reaction with a nitroxide consists in blocking the growing free-radical species in the form of a bond of C—$ONR_1R_2$ type, $R_1$ and $R_2$ possibly being, independently of each other, an alkyl radical containing from 2 to 30 carbon atoms, or together forming, with the nitrogen atom, a ring containing from 4 to 20 carbon atoms, such as, for example, a 2,2,6,6-tetramethylpiperidyl ring. This polymerization technique is especially described in the articles "Synthesis of nitroxy-functionalized polybutadiene by anionic polymerization using a nitroxy-functionalized terminator" published in *Macromolecules* 1997, Volume 30, pages 4238-4242, and "Macromolecular engineering via living free radical polymerizations" published in *Macromol. Chem. Phys.* 1998, Vol. 199, pages 923-935, or in patent application WO-A-99/03894.

The technique of RAFT (reversible addition-fragmentation chain-transfer) polymerization consists in blocking the growing free-radical species in the form of a bond of C—S type. Dithio compounds such as thiobenzoates, dithiocarbamates or xanthan disulphides are used to do this. This technique is described especially in patent application WO-A-98/58974 and in the article "A more versatile route to block copolymers and other polymers of complex architecture by living radical polymerization: the RAFT profess", published in *Macromolecules*, 1999, Volume 32, pages 2071-2074.

Second Mode:

The block polymers according to the invention may also be obtained by using the standard free-radical polymerization technique by casting the monomers sequentially. In this case, only control of the nature of the blocks is possible (no control of the masses).

This involves polymerizing, in a first stage, a monomer M1 in a polymerization reactor and monitoring, by kinetics, its consumption over time and then, when M1 is about 95% consumed, introducing a new monomer M2 into the polymerization reactor.

A polymer of block structure of M1-M2 type is thus readily obtained.

The invention also relates to cosmetic or pharmaceutical compositions comprising the copolymer of specific structure as described above.

Generally, these compositions contain from 0.1% to 60% by weight, preferably from 0.5% to 50% by weight and more preferably from 1% to 40% by weight of the copolymer according to the invention.

These cosmetic compositions according to the invention comprise, besides the said polymers, a physiologically acceptable medium, i.e. a medium that is compatible with keratin materials, for instance the skin, the hair, the eyelashes, the eyebrows and the nails.

In general, it should be considered that the whole composition is physiologically acceptable.

The said physiologically acceptable medium generally comprises a physiologically acceptable suitable solvent, in which the copolymer according to the invention is in dissolved or dispersed form.

The composition may thus comprise, as solvent forming a hydrophilic phase, water or a mixture of water and of hydrophilic organic solvent(s), for instance alcohols and especially linear or branched lower monoalcohols containing from 2 to 5 carbon atoms, for instance, ethanol, isopropanol or n-propanol, and polyols, for instance glycerol, diglycerol, propylene glycol, sorbitol, pentylene glycol and polyethylene glycols. The hydrophilic phase may also contain hydrophilic $C_2$ ethers and $C_2$-$C_4$ aldehydes.

Water or a mixture of water and of hydrophilic organic solvents may be present in the composition according to the invention in an amount ranging from 0% to 99% (especially 0.1 to 99%) by weight, and preferably from 10% to 80% by weight, relative to the total weight of the composition.

The composition may also comprise a fatty phase consisting especially of fatty substances that are liquid at room temperature (in general 25° C.) and/or fatty substances that are solid at room temperature, such as waxes, pasty fatty substances and gums, and mixtures thereof. These fatty substances may be of animal, plant, mineral or synthetic origin. This fatty phase may also contain lipophilic organic solvents.

As fatty substances that are liquid at room temperature, often known as oils, which may be used in the invention, mention may be made of: hydrocarbon-based oils of animal origin such as perhydrosqualene, hydrocarbon-based plant oils such as liquid triglycerides of fatty acids containing from 4 to 10 carbon atoms, for instance heptanoic or octanoic acid triglyceride, or alternatively sunflower oil, corn oil, soybean oil, grape seed oil, sesame seed oil, apricot oil, macadamia oil, castor oil, avocado oil, caprylic/capric acid triglycerides, jojoba oil and karite butter; linear or branched hydrocarbons of mineral or synthetic origin such as liquid paraffins and derivatives thereof, petroleum jelly, polydecenes and hydrogenated polyisobutene such as parleam; synthetic esters and synthetic ethers, especially of fatty acids, such as, for example, purcellin oil, isopropyl myristate, 2-ethylhexyl palmitate, 2-octyldodecyl stearate, 2-octyldodecyl erucate and isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate or diethylene glycol diisononanoate; and pentaerythritol esters; fatty alcohols containing from 12 to 26 carbon atoms, for instance octyldodecanol, 2-butyloctanol, 2-hexyldecanol, 2-undecylpentadecanol and oleyl alcohol; partially hydrocarbon-based or silicone-based fluoro oils; silicone oils, for instance linear or cyclic, volatile or nonvolatile polydimethylsiloxanes (PDMSs) that are liquid or pasty at room temperature, for instance cyclomethicones, dimethicones, optionally comprising a phenyl group, for instance phenyl trimethicones, phenyltrimethylsiloxydiphenyl siloxanes, diphenylmethyldimethyltrisiloxanes, diphenyl dimethicones, phenyl dimethicones and polymethylphenylsiloxanes; mixtures thereof.

These oils may be present in a content ranging from 0.01% to 90% and better still from 0.1% to 85% by weight, relative to the total weight of the composition.

The composition according to the invention may also comprise one or more organic solvents that are cosmetically acceptable (acceptable tolerability, toxicology and feel).

These solvents may generally be present in a content ranging from 0% to 90%, preferably from 0.1% to 90% and more preferably from 10% to 90% by weight, and better still from 30% to 90%, relative to the total weight of the composition.

As solvents that may be used in the composition of the invention, mention may be made of acetic acid esters, for instance methyl acetate, ethyl acetate, butyl acetate, amyl acetate, 2-methoxyethyl acetate or isopropyl acetate; ketones, for instance methyl ethyl ketone or methyl isobutyl ketone; hydrocarbons, for instance toluene, xylene, hexane or heptane; aldehydes containing from 5 to 10 carbon atoms; ethers containing at least 3 carbon atoms; and mixtures thereof.

The waxes may be hydrocarbon-based waxes, fluoro waxes and/or silicone waxes and may be of plant, mineral, animal and/or synthetic origin. In particular, the waxes have a melting point of greater than 25° C. and preferably greater than 45° C.

As waxes that may be used in the composition of the invention, mention may be made of beeswax, carnauba wax or candelilla wax, paraffin, microcrystalline waxes, ceresin or ozokerite; synthetic waxes, for instance polyethylene waxes or Fischer-Tropsch waxes, or silicone waxes, for instance alkyl dimethicones or alkoxy dimethicones containing from 16 to 45 carbon atoms.

The gums are generally polydimethylsiloxanes (PDMSs) of high molecular weight or cellulose gums or polysaccharides and the pasty substances are generally hydrocarbon-based compounds, for instance lanolins and derivatives thereof, or PDMSs.

The nature and amount of the solid substances depend on the desired mechanical properties and textures. As a guide, the composition may contain from 0 to 50% by weight and better still from 1% to 30% by weight of waxes, relative to the total weight of the composition.

The polymer may be combined with one or more auxiliary film-forming agents. Such a film-forming agent may be chosen from any compound known to those skilled in the art as being capable of fulfilling the desired function, and may be chosen especially from plasticizers and coalescers.

The composition according to the invention may also comprise one or more dyestuffs chosen from water-soluble dyes and pulverulent dyestuffs, for instance pigments, nacres and flakes that are well known to those skilled in the art. The dyestuffs may be present in the composition in a content ranging from 0.01% to 50% by weight and preferably from 0.01% to 30% by weight, relative to the weight of the composition.

The term "pigments" should be understood as meaning white or coloured, mineral or organic particles of any form, which are insoluble in the physiological medium and which are intended to colour the composition.

The term "nacres" should be understood as meaning iridescent particles of any form, produced especially in the shell of certain molluscs, or alternatively synthesized.

The pigments may be white or coloured, and mineral and/or organic. Among the mineral pigments that may be mentioned are titanium dioxide, optionally surface-treated, zirconium oxide or cerium oxide, and also zinc oxide, iron oxide (black, yellow or red) or chromium oxide, manganese violet, ultramarine blue, chromium hydrate and ferric blue, and metal powders, for instance aluminium powder or copper powder.

Among the organic pigments that may be mentioned are carbon black, pigments of D & C type, and lakes based on cochineal carmine or on barium, strontium, calcium or aluminium.

The nacreous pigments may be chosen from white nacreous pigments such as titanium-coated mica or bismuth oxychloride-coated mica, coloured nacreous pigments such as titanium mica coated with iron oxides, titanium mica coated especially with ferric blue or with chromium oxide, titanium mica coated with an organic pigment of the abovementioned type and also nacreous pigments based on bismuth oxychloride.

The water-soluble dyes are, for example, beetroot juice or methylene blue.

The composition according to the invention may also comprise one or more fillers, especially in an amount ranging from 0.01% to 50% by weight and preferably ranging from 0.01% to 30% by weight, relative to the total weight of the composition. The term "fillers" should be understood as meaning colourless or white, mineral or synthetic particles of any form, which are insoluble in the medium of the composition, irrespective of the temperature at which the composition is manufactured. These fillers serve especially to modify the rheology or texture of the composition.

The fillers may be mineral or organic of any form, platelet, spherical or oblong, irrespective of the crystallographic form (for example leaflet, cubic, hexagonal, orthorhombic, etc.). Mention may be made of talc, mica, silica, kaolin, polyamide powder (Nylon®) (Orgasol® from Atochem), poly-β-alanine powder and polyethylene powder, tetrafluoroethylene polymer (Teflon®) powders, lauroyllysine, starch, boron nitride, hollow polymer microspheres such as those of polyvinylidene chloride/acrylonitrile, for instance Expancel® (Nobel Industrie) or of acrylic acid copolymers (Polytrap® from the company Dow Corning) and silicone resin microbeads (for example Tospearls® from Toshiba), polyorganosiloxane elastomer particles, precipitated calcium carbonate, magnesium carbonate, magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

The composition according to the invention may also contain ingredients commonly used in cosmetics, such as vitamins, thickeners, trace elements, softeners, sequestering agents, fragrances, acidifying or basifying agents, preserving agents, sunscreens, surfactants, antioxidants, agents for preventing hair loss, antidandruff agents and propellants, or mixtures thereof.

Needless to say, a person skilled in the art will take care to select this or these optional additional compound(s), and/or the amount thereof, such that the advantageous properties of the composition corresponding to the invention are not, or are not substantially, adversely affected by the envisaged addition.

The composition according to the invention may especially be in the form of a suspension, a dispersion, a solution, a gel, an emulsion, especially an oil-in-water (O/W) or water-in-oil (W/O) emulsion, or a multiple emulsion (W/O/W or polyol/O/W or O/W/O emulsion), in the form of a cream, a paste, a mousse, a dispersion of vesicles, especially of ionic or non-ionic lipids, a two-phase or multi-phase lotion, a spray, a powder, a paste, especially a soft paste (especially a paste having a dynamic viscosity at 25° C. of about from 0.1 to 40 Pa·s at a shear rate of 200 $s^{-3}$ after measurement for 10 minutes in cone/plate geometry). The composition may be anhydrous, for example it may be an anhydrous paste.

A person skilled in the art may select the appropriate presentation form, and also the method for preparing it, on the basis of his general knowledge, taking into account firstly the nature of the constituents used, especially their solubility in the support, and secondly the intended use of the composition.

The composition according to the invention may be a makeup composition, for instance complexion products (foundations), rouges, eye shadows, lip products, concealer products, blushers, mascaras, eyeliners, eyebrow makeup products, lip pencils, eye pencils, nail products, such as nail varnishes, body makeup products or hair makeup products (hair lacquer or mascara).

The composition according to the invention may also be a hair product, especially for holding the hairstyle or for shaping the hair. The hair compositions are preferably shampoos, hairsetting gels or lotions, blow-drying lotions, or fixing and styling compositions such as lacquers or sprays.

The lotions may be packaged in various forms, especially in vaporizers, in pump-dispenser bottles or in aerosol containers in order to allow the composition to be applied in vaporized form or in the form of a mousse. Such packaging forms are indicated, for example, when it is desired to obtain a spray or a mousse for fixing or treating the hair.

The invention will now be described with reference to the following examples, which are given as non-limiting illustrations.

EXAMPLES

Example 1

Preparation of a Difunctional Polymerization Initiator

A difunctional initiator is prepared according to the following reaction scheme:
THF/triethylamine

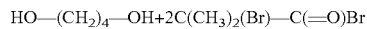

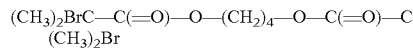

To do this, 18 g (0.2 mol) of 1,4-butanediol are mixed with 100 g of tetrahydrofuran and the mixture is allowed to equilibrate for 10 minutes at room temperature. 40.4 g (0.4 mol) of triethylamine are then added slowly, over a period of 30 minutes, so that the temperature of the solution does not rise suddenly. 92 g (0.4 mol) of 2-bromoisobutyryl bromide are then added very slowly, over a period of 3 hours, and with cooling to 5° C. During this addition, a gradual yellowing of the reaction solution is observed. Stirring is continued overnight at 25° C. and the temperature is then allowed to rise gradually to room temperature.

The reaction solution is concentrated by evaporating off the THF and the residue is precipitated in water. The aqueous phase is then extracted three times with ethyl ether, and the ether phase is then dried over magnesium sulphate.

After evaporating off the ether, 63 g of bis(n-butyl 1,4-bromoisobutyrate) are thus obtained, which corresponds to a yield of 80%.

Example 2

Preparation of a poly(methyl acrylate-b-butyl acrylate-b-methyl acrylate) triblock copolymer Step I: Polymerization of n-butyl acrylate, Tg=−50° C.

1.43E-03 mol, i.e. 5.54E-01 g, of difunctional initiator prepared in Example 1, 2.86E-03 mol, i.e. 4.10E-01 g of CuBr, 7.81E-01 mol, i.e. 100 g, of butyl acrylate and 2.86E-03 mol, i.e. 4.95E-01 g, of N,N,N',N'',N''-pentamethyldiethylenetriamine are mixed together in a hermetic reactor comprising a nitrogen inlet and protected from oxygen.

The mixture is heated, under a nitrogen atmosphere, to a temperature of 90° C., the nitrogen inlet is closed and the temperature is maintained for 7 hours 30 minutes, resulting in the production of a solution of the polymer.

This solution of the polymer is passed through a bed of neutral alumina and the clear solution is then precipitated in 5 volumes of a methanol/water mixture (80/20).

Step II: Polymerization of methyl acrylate, Tg=+10° C.

1.31E-04 mol, i.e. 10.5 g, of the above macroinitiator: functional polybutyl acrylate, 2.62E-04 mol, i.e. 2.59E-02 g of CuBr, 8.40 ml of diphenyl diether solvent, 2.62E-04 mol, i.e. 4.53E-02 g, of N,N,N',N'',N''-pentamethyldiethylenetriamine and 3.93E-02 mol, i.e. 3.39 g, of methyl acrylate monomer are mixed together in a hermetic reactor comprising a nitrogen inlet and protected from oxygen.

The mixture is reacted for 4 hours at 90° C. and is then allowed to cool to room temperature. The solution is dissolved in about 100 ml of dichloromethane. This solution of the polymer is passed through a bed of neutral alumina and the clear solution is then precipitated in 5 volumes of a methanol/water mixture (80/20).

6 g of polymer in the form of a paste are obtained, which corresponds to a yield of 43% by weight.

The paste is washed with hot heptane to remove therefrom any residual monomers present.

The weight-average and number-average molar mass are determined by gel permeation liquid chromatography (THF solvent, calibration curve established with linear polystyrene standards).

The number-average molar mass ($M_n$) is equal to 88,000 g/mol and the weight-average molar mass ($M_w$) is equal to 102,000 g/mol.

The copolymer has two glass transition temperatures $T_g$, the first equal to −47° C. attributable to the poly(butyl acrylate) block, and the second equal to 10° C., attributable to the poly(methyl acrylate) blocks.

The "tack" value for this polymer, measured by the method described above, is 3.5 N.

Example 3

Preparation of a Lacquer

An aerosol is prepared with 100 g of a solution at 9% by weight of the copolymer prepared in Example 2 in ethanol and 75 g of dimethyl ether acting as propellent gas.

The composition is sprayed onto locks of chestnut-coloured hair 18 cm long, and the hold of the hairstyle and the supple appearance of the locks are evaluated by a panel of 5 individuals, using a grading scale ranging from 0 (poor) to 5 (excellent).

The grades obtained are 4 for the hold of the hairstyle and 4 for the supple appearance of the locks.

Example 4

Preparation of a "Basecoat" for a Nail Varnish

The copolymer is dissolved in ethyl acetate: the polymer content of the solution obtained is 25% by weight. The copolymer solution of Example 2 is applied to a nail. After drying for 10 minutes, a standard solvent-based nail varnish is applied.

The strength of the varnish and the impact strength are improved.

The invention claimed is:

1. A cosmetic composition, comprising a linear, block ethylenic copolymer dissolved in a physiologically acceptable medium, wherein the linear, block ethylenic copolymer comprises:
   at least two blocks having different glass transition temperatures, Tg;
   at least one of these blocks having a glass transition temperature of 20° C. to −100° C.;
   said copolymer also having an adhesion or tack value of greater than 1 N
   wherein the at least one block with a Tg of 20° C. to −100° C. is a copolymer of different monomers, and wherein homopolymers prepared from these monomers have glass transition temperatures of 20° C. to −100° C., wherein the monomers are selected from the group consisting of
   acrylates of formula $CH_2$=$CHCOOR_1$, wherein $R_1$ is a linear or branched unsubstituted 1 to 12C alkyl group;

methacrylates of formula $H_2C=C(CH_3)$—$COOR_2$, wherein $R_2$ is a linear or branched unsubstituted 3 to 12 C alkyl group.

2. The composition according to claim 1, wherein the linear, block ethylenic copolymer is a film-forming copolymer.

3. The composition according to claim 1, wherein the adhesion or tack value of the linear, block ethylenic copolymer is greater than 2N.

4. The composition according to claim 3, wherein the adhesion or tack value of the linear, block ethylenic copolymer is greater than 3N.

5. The composition according to claim 1, wherein the difference in glass transition temperatures, Tg between the at least two blocks having different glass transition temperatures in the linear, block ethylenic copolymer is from 40 to 120° C.

6. The composition according to claim 5, wherein the difference in glass transition temperatures, Tg between the at least two blocks having different glass transition temperatures in the linear, block ethylenic copolymer is from 40 to 110° C.

7. The composition according to claim 5, in which the difference in glass transition temperatures, Tg, between the at least two blocks having different glass transition temperatures in the linear, block ethylenic copolymer is from 40 to 100° C.

8. The composition according to claim 1, wherein the number-average mass of the linear, block ethylenic copolymer is from 10,000 to 500,000 g/mol.

9. The composition according to claim 1, wherein the at least one block with a Tg of 20° C. to 100° C. in the linear, block ethylenic copolymer is present in an amount of from 99% to 40% by mass of the linear, block ethylenic copolymer.

10. The composition according to claim 9, wherein the at least one block with a Tg of 20° C. to −100° C. in the linear, block ethylenic copolymer is present in an amount from 95% to 55% by mass of the linear, block ethylenic copolymer.

11. The composition according to claim 1, wherein the at least one block with a Tg of 20° C. to −100° C. in the linear, block ethylenic copolymer has a Tg from 20° C. to −95° C.

12. The cosmetic composition according to claim 1, comprising from 0.1% to 60% by weight of the copolymer.

13. The cosmetic composition according to claim 1, wherein the physiologically acceptable medium comprises one or more suitable solvents forming a hydrophilic phase, wherein the one or more suitable solvents is selected from the group consisting of water, hydrophillic organic solvent, alcohol, linear lower monoalcohols having from 2 to 5 carbon atoms, branched lower monoalcohols having from 2 to 5 carbon atoms, ethanol, isopropanol, n-propanol, polyol, glycerol, diglycerol, propylene glycol, sorbitol, pentylene glycol and polyethylene glycol.

14. The cosmetic composition according to claim 13, wherein the hydrophilic phase further comprises hydrophilic $C_2$ ethers, $C_2$ to $C_4$ aldehydes, or mixtures thereof.

15. The cosmetic composition according to 14, wherein said physiologically acceptable medium further comprises a fatty phase comprising fatty substances that are liquid or solid at room temperature, wherein the fatty substances are of animal, plant, mineral or synthetic origin.

16. The cosmetic composition according to claim 15, further comprising one or more cosmetically acceptable organic solvents.

17. The cosmetic composition according to claim 16, wherein said physiologically acceptable medium further comprises one or more auxiliary film-forming agents selected from the group consisting of a plasticizer and coalescer.

18. The cosmetic composition according to claim 1, further comprising one or more dyestuffs selected from the group consisting of a water-soluble dye and pulverulent dyestuff, pigment, nacre, and flake.

19. The composition according to claim 1, further comprising fillers.

20. The cosmetic composition according to claim 1, further comprising one or more ingredients selected from the group consisting of a vitamin, thickener, grace element, softener, sequestering agent, fragrance, acidifying agent, basifying agent, preserving agent, sunscreen, surfactant, antioxidant, agent for preventing hair loss, antidandruff agent, propellant, and mixtures thereof.

21. The cosmetic composition according to claim 1, which is in a form selected from the group consisting of a suspension, a dispersion, a solution, a gel, an emulsion, an oil-in-water emulsion, a water-in-oil emulsion, and a multiple emulsion.

22. The cosmetic composition according claim 1, which is a product selected from the group consisting of a hair product, a lacquer, and a shampoo.

23. The cosmetic composition according to claim 1, wherein the composition is selected from the group consisting of a makeup composition and a nail varnish.

24. A process for making up or caring for keratin materials, comprising contacting the cosmetic composition according to claim 1 to the keratin materials.

25. A method to improve the styling power and the hold of a hair lacquer, comprising
    contacting the composition according to claim 1 with the hair lacquer.

26. A method to increase the adhesion of a nail varnish, comprising
    contacting the composition according to claim 1 with the nail varnish.

27. A method to improve the hold and adhesion of a makeup composition, comprising
    contacting the composition according to claim 1 with the makeup composition.

* * * * *